United States Patent [19]
Koga et al.

[11] Patent Number: 5,281,577
[45] Date of Patent: Jan. 25, 1994

[54] INHIBITOR OF THE PROLIFERATION OF HERPES VIRUSES AND INHIBITOR OF THE RECURRENCE OF AFFECTIONS CAUSED BY THEIR LATENT INFECTION

[75] Inventors: Junichi Koga, Kobe; Yasuhiro Ohashi, Noda; Hajime Hiratani, Sennan, all of Japan

[73] Assignees: JCR Pharmaceuticals Co., Ltd., Hyogo; Noda Shokukin Kogyo Co., Ltd., Chiba, both of Japan

[21] Appl. No.: 962,022

[22] Filed: Oct. 15, 1992

Related U.S. Application Data

[63] Continuation of Ser. No. 831,079, Feb. 5, 1992, abandoned, which is a continuation of Ser. No. 638,189, Jan. 7, 1991, abandoned.

[30] Foreign Application Priority Data

Jan. 10, 1990 [JP]  Japan .................................. 2-3818

[51] Int. Cl.⁵ .................. A61K 37/02; A61K 35/84

[52] U.S. Cl. .................................. 514/2; 424/195.11; 530/371

[58] Field of Search .................. 514/2; 424/195.1; 530/371

[56]         References Cited
        U.S. PATENT DOCUMENTS 4,185,097  1/1980  Ward et al. ................. 424/195.1

OTHER PUBLICATIONS

Suzuki et al. Biochemical and Biophysical Research Communications, vol. 160, No. 1, 1989 pp. 367–373.

Primary Examiner—Michael G. Wityshyn
Assistant Examiner—Choon P. Koh
Attorney, Agent, or Firm—Burgess, Ryan & Wayne

[57]            ABSTRACT

An inhibitor of the proliferation of herpesviruses and of the recurrence of affections caused by their latent infection, which is an active material obtained by fractional purification of the aqueous extract from cultured *Lentinus edodes* mycelia.

3 Claims, 1 Drawing Sheet

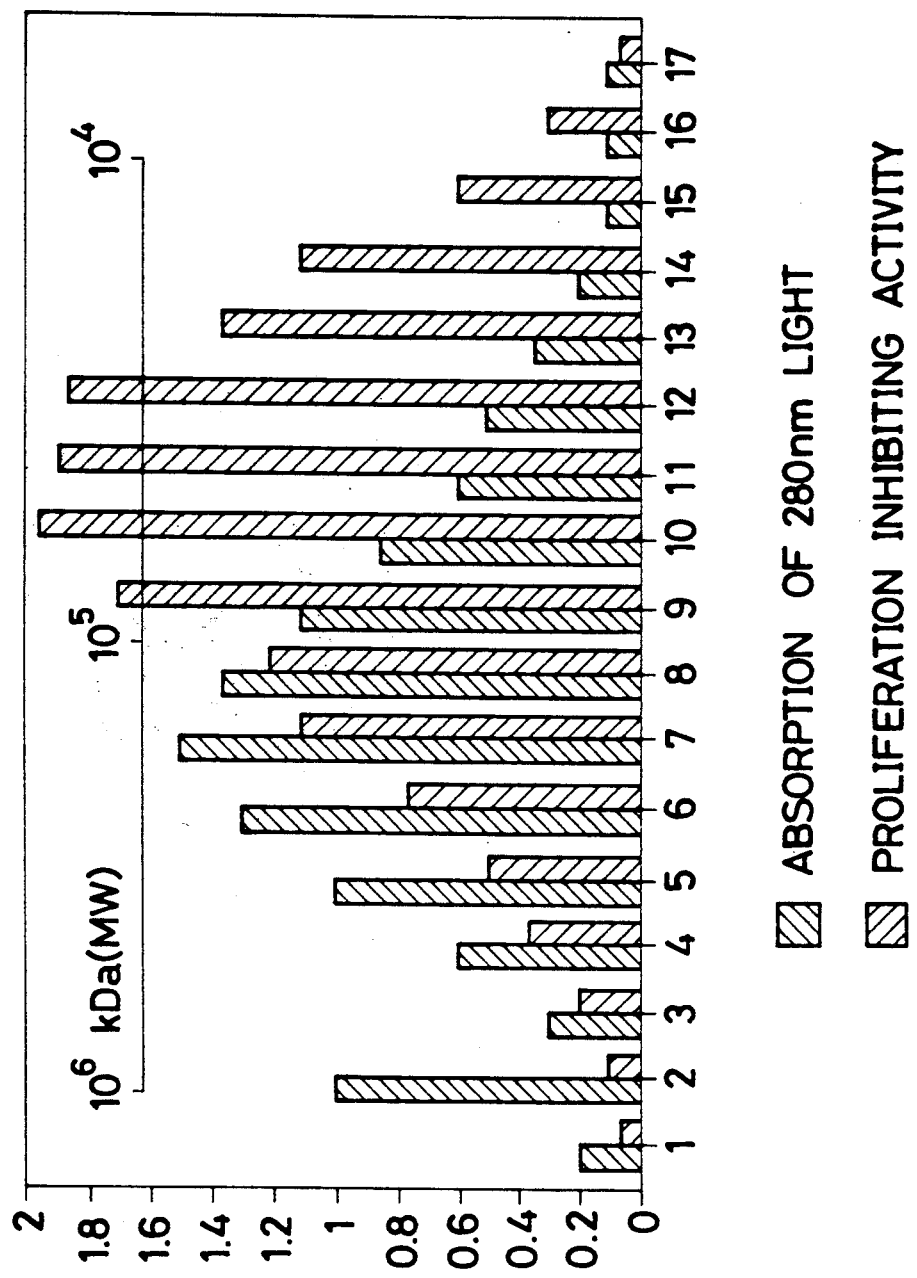

INHIBITOR OF THE PROLIFERATION OF HERPES VIRUSES AND INHIBITOR OF THE RECURRENCE OF AFFECTIONS CAUSED BY THEIR LATENT INFECTION

This application is a continuation of application Ser. No. 07/831,079, filed Feb. 5, 1992, now abandoned, which is a continuation of application Ser. No. 07/638,189, filed Jan. 7, 1991, now abandoned.

FIELD OF INVENTION

The present invention relates to an inhibitor of the proliferation of herpesviruses in cells infected with them and of the reactivation of latent herpesviruses and the reinfection following it in a living body which has received a latent infection characteristic of these viruses.

BACKGROUND OF THE INVENTION

The human herpesvirus is a typical envelop virus having double-stranded DNA in its nucleocapsid, and is known to cause a variety of affections to an organism infected with it. In this category of human herpesviruses, these viruses are known: herpes simplex viruses type 1 and 2 (HSV1 and 2), varicella-herpes zoster viruses (VZV), cytomegaloviruses (CMV), Epstein-Barr viruses (EBV) and human herpesvirus type 6 (HHV6).

These viruses are characterized in that after a living body is infected with them first in its early childhood, they infect it latently, that is, continue to be alive as long as the living body lives. As the immunity of the organism changes, their affection recurs and is cured repeatedly throughout its life. In this course, some affections caused by the viruses are so grave that their infected living bodies die. Concerning immunosuppression during organ transplantation, the reinfection and reactivation of this virus affect the result of the operation of organ transplantation itself, so the development of an antiviral agent against herpesviruses is urgently needed for such operations.

This virus is also known for its causing a fatal affection or a sequela such as cerebritis to a fetus or newborn child by infection of mother and fetus by way of transplacental infection. More and more details are known of its relation with the manifestation of symptoms of venereal diseases such as genital herpes (herpes simplex virus type 2), epipharynx cancer, Burkitt lymphoma (EB virus), Kaposi sarcoma (CMV) and AIDS (HHV6). Recently in the course of development molecular biology has made a large number of discoveries related to herpesvirus components. Information has been growing in amount on the mechanism and role of glycoprotein specific to these viruses, enzyme activity in them such as thymidine kinase activity, the characteristic mechanism of genome DNA, latent infection, the base sequences related to the canceration of cells and so forth. However, many points remain to be explained in connection with herpesviruses' life cycle seen in the relation among this virus, its infected cell and the immunity of the organism during latent infection and reinfection, being part of the obstacles to developing an inhibitor against the virus.

As understood from the above, this virus is a dangerous one which has very high pathogenicity, and thus a therapeutic agent against it is urgently needed. However, aciclovir is the only remedy now in use. To make matters worse, the application of the remedy is limited, since the possibility cannot be denied that it has a side effect such as teratogenic effect etc. because it is an antagonist to nucleic acid synthesis.

Since olden times, various physiological active substances arising from mushrooms have been known, and some are used today as medicine. For example, Klestin (Yanagawa et al., Cancer and Chemotherapy 11, 2155, 1985), Lentinan (Suga et al., Cancer Research 44, 5162, 1984), Shizofiran are used as antitumor agents. The active principles of these agents are polysaccharides or glycoprotein arising from bacteria, and their effect is thought to be given by a biological response modifier (BRM) stimulating the immune system of a living body. These agents have no directly antiviral effect.

Recently, it has been reported that pllysaccharides having sulfuric acid radicals, for instance dextran sulfuric acid, show antiviral activity against AIDS viruses (Mitsuya et al., Science 240, 646, 1988). Further, Tochikura and his group suggest that the LEM which is hot water extract of cultured Lentinus edodes mycelia (Med. Microboil. Immunol. 177, 235, 1988) has the same kind of activity. However, these have been nothing but infection inhibiting activity shown in vitro in the inhibition of the absorption of viruses to cells or of the fusion of infected cells with normal cells.

The method of producing the LEM is already described in Japanese Patent Application Laid-Open No. 53-10117. Various kinds of activity in vivo shown by the LEM have been disclosed. This material has been in use as pesticide against the infection with tobacco mosaic viruses. It has been reported to have clinical effect against hepatitis. The LEM is known to be made up of a mixture or complex of polysaccharides whose principal constituent is xylose and arabinose, water-soluble lignin and peptide and diverse inorganic substances, so has a long record of use as health food. With regard to origin as well as constitution, it has an entirely different property from that of Klestin, Lentinan and Shizofiran whose active constituents are conventional chemicals such as glucan and glycoproten.

As described earlier, human herpesviruses cause a grave affection, but their remedies are too few and their application is limited. The development of a therapy for affections caused by these viruses and of a therapeutic agent against them is, therefore, a very pressing problem.

Agents in current use against the viruses, aciclovir and BV-araU which is at present being clinically experimented with are analogues of nucleic acid, and target an enzyme existing in a nucleic acid synthesis system specific to the viruses in order to inhibit the nucleic acid synthesis. However, this does not necessarily work without affecting the nucleic acid synthesis system on the side of the living body. They are really chemicals whose side effects cannot be denied. Thus, a safer and more effective medical agent is required today.

The object of the present invention is, therefore, to provide a safe and entirely new therapeutic agent different from conventional antiviral agents against herpesviruses, which is for inhibiting the proliferation of herpesviruses in cells and the reactivation of and the reinfection with these viruses in an organism which has received a latent infection with the viruses.

SUMMARY OF THE INVENTION

The inventors of the present invention discovered in the LEM which is the starting material for the present active material or in its fractions the presence of fractions having absorption inhibiting activity against herpes simplex viruses, and applied for a patent (on Feb. 10, 1989). In the course of our further research, we found that one of the fractions obtained by purification processes starting with the LEM, to our surprise, had the activity for inhibition of the proliferation of these viruses in cells. The inventors also found that their reactivation was inhibited by intraperitoneal administration of this fraction (100 μg per day for 4 days) to a mouse which had received latent infection with them. In addition, their activation was inhibited by giving this fraction orally (500 μg per day for 5 days) to a mouse similarly infected. This was utterly unexpected to the inventors. Considering the constituents of the fraction to be macromolecules (10,000 to 1,000,000 dalton) and its antigenicity, it seems difficult to devise any other medical application of this substance than oral administration and external use, so this experimental result was a very important discovery in terms of clinical application. Incidentally, an experiment on acute toxicity showed that this agent has a low toxicity: $LD_{50} = 15$ g per day (rat and mouse).

The inventors of the active material named it JLS-18. It arises by fractionation from the LEM which is warm water extract of cultured *Lentinus edodes* mycelia. The method of producing the LEM is detailed in the process described in Japanese Patent Application Laid-Open No. 53-10117. According to this method, *Lentinus edodes* mycelia are cultured in a medium made of bagasse and rice bran, and then warm water extraction of the active principle of the mycelia that are just before the forming of fruit-bodies obtain the LEM. By fractionating this LEM as a starting liquid, JLS-18 is fractionated. The method of fractionation is carried out in the combination of salting out, precipitation with organic solvent, ion exchange chromatography, hydrophobic chromatography and gel filtration chromatography. JLS-18, an active material thus obtained has constant analytical values for carbohydrate composition, amino acid composition and lignin ratio, which suggests that these three constituents form a complex with their proportions constant. Since the molecular weight of this material ranges from several hundred to several million dalton according to the polymerization degrees of lignin forming the framework of the material, it is difficult to specify the molecular weight of the material. However, antiviral activity is strongest with the material weighing from a ten thousand to a hundred thousand dalton. Thus, material having such molecular weight is thought to achieve the objective of an antiviral agent against herpesviruses which is in accordance with the present, invention.

BRIEF DESCRIPTION OF THE INVENTION

FIG. 1 is a graphical representation of the result of an examination, carried out in Example 2, of virus inhibiting activity exhibited by molecular weight fractions obtained in example 1.

The present invention is based upon the above-mentioned findings, and is embodied by an inhibitor of the proliferation of herpesviruses which contains JLS-18 and by an inhibitor, which also contains JLS-18, of the reactivation of and the reinfection with these viruses with which a living body has received a latent infection. These medical agents can be applied externally or by oral administration. As for external use, it is preferable to have JLS-18 in pharmaceutical forms suitable for local administration to a region evidently or possibly infected with herpesviruses. Likely skin or membrane locations are on openings such as an oral cavity, pharynx, nasal cavity, eyelid, anus, rectum, urethra and vagina, wounds of the body or their periphery. An external use agent according to the present invention is for administration in pharmaceutical forms such as suppositories, troches, jelly, cream, cataplasms, ointment, plaster, liniment, solution, nebulae, aerosol and external use powder from which selections are to be made according to the necessity. These external use medical agents are prepared by known methods. Since JLS-18 is very stable, its conservation is easy after it is dispensed as an external use agent.

JLS-18, an agent of the present invention is effective as an inhibitor of herpesvirus reactivation and of reinfection following it when taken on the occasion of such reactivation or for the purpose of preventing it from occurring. Because of the high stability of JLS-18, there is no limitation to the selection for its pharmaceutical form from powder, granules, pills, tabellae, spirit, lemonades, etc.

JLS-18 is preferably used in such a way that an external use agent is constituted of about 0.01 to 1% of JLS-18. For oral administration, 10 mg to 10 g a day is desirable.

The agent JLS-18 in accordance with the present invention not only inhibits herpesviruses from being bound to their target cells but inhibits their proliferation in cells, thus preventing the manifestation of diseases of their origin and the increase of infected regions in number and area. Further, the oral administration of this agent allows preventing the reactivation of herpesviruses with which an organism has received a persistent or latent infection, and also helps to alleviate symptoms after the reinfection with these viruses.

The following examples are further illustrative of the present invention.

EXAMPLE 1

JLS-18 was derived from LEM by purification, first by adding 1 L of 50 mM phosphate buffer solution (pH 7.4) containing 2M ammonium sulfate to 1 L of the LEM liquid, vigorously stirring the mixture and filtering it with a 0.45 μm film. Then, the filtrate was passed through Phenyltoyopearl (Toso) buffered by means of a 50 mM phosphate buffer solution (pH 7.4) containing 1M ammonium sulfate. Absorbed antiviral activity constituents were fractionated while at the same time salt concentration was lowered gradually. As a result of this chromatography, the most hydrophobic fractions of the activity constituents were eluted within the range of phosphate concentration not more than 10 mM. After concentrated by freeze-drying, these fractions were applied to molecular weight fractionation by gel filtration using HW-55 (Toso). Each fraction obtained was examined for the antiviral activity (proliferation inhibiting activity) as described in Example 2, and we called a fraction (range) exhibiting the greatest activity as shown below by the name JLS-18. The result of the analysis of this agent is detailed in the table below, that of the chromatography in FIG. 1 together with the result of the examination carried out in Example 2. Antiviral activity was distributed widely among the fractions obtained by the molecular weight fractionation, and this activity was greatest within the range of molecular weight 10,000 to 100,000 dalton. Then, the fractions having such molecular weight were desalted and freeze-dried.

Analytical values for JLS-18 were as follows:

(1) Constitution (%)

| Protein | 10 to 20 |
|---|---|
| Carbohydrate | 15 to 30 |
| Lignin | 65 to 75 |

(2) Amino acid constitution in the protein (%)

| Asx | 15.0–16.5 | Met | 0.3–0.7 |
|---|---|---|---|
| Thr | 6.5–7.2 | Ile | 3.8–4.9 |
| Ser | 6.5–7.3 | Leu | 4.9–6.6 |
| Glx | 15.0–17.5 | Tyr | 1.1–1.5 |
| Pro | 6.8–8.0 | Phe | 3.0–4.6 |
| Gly | 9.3–11.0 | Lys | 3.6–4.8 |
| Ala | 7.3–8.8 | His | 2.3–2.9 |
| Val | 5.9–6.5 | Arg | 0.7–1.1 |

(3) Carbohydrate constitution (%)

| Glucose | 35 to 55 |
|---|---|
| Xylose | 29 to 41 |
| Galactose | 2 to 7 |
| Arabinose | 12 to 20 |
| Mannose | 1 to 4 |

EXAMPLE 2

The manner in which virus proliferation inhibiting activity was assayed will be described here. First, the BS-C-1 cell, which is a cell line derived from a monkey's kidney, was multiplied in the minimal essential medium (MEM) (Nissui Pharmaceutical Co.) containing 10% fetal calf serum (Flow Corp.) in a Petri dish 30 mm in diameter (Corning Corp.). And then fractions obtained by molecular fractionation as shown in Example 1 were diluted ten times each in the MEM containing 10% fetal calf serum so as to be used as samples, and the cells in the Petri dish were cultured in the medium that contains each of the diluted fractions for 24 hours. A diluent of 100 Plaque forming unit (PFU) per milliliter of herpes simplex viruses was prepared by using a medium containing 2% fetal calf serum. After the cells were rinsed with Dalbecco's PBS, 0.5 ml of the herpes simplex virus diluent was pipetted into each Petri dish and maintained at 37° C. for two hours to absorb the viruses to the cells. After absorption, these cells were rinsed with PBS again, and 2 ml of the MEM containing fresh 2% fetal calf serum was pipetted into each dish for 48 hours of culture. The cultured viruses were then processed by a 3000 rpm centrifuge together with the cells for 10 minutes so that the supernatant fluid might be recovered from the content of each dish. The number of viruses in these supernatant fluids was evaluated by using the plaque technique. This plaque technique was employed in the way described in Example 3.

FIG. 1 is a graphical representation of the result of an examination, carried out in Example 2, of virus inhibiting activity exhibited by molecular weight fractions obtained in Example 1. This bar graph shows absorption of 280 nm light by each of the fractions 1 to 17 and herpesvirus proliferation inhibiting activity. Molecular weight estimated from the elution by gel filtration is shown in the upper part of the drawing.

EXAMPLE 3

Fractions obtained as described in Example 1 were applied to bioassay. When a mouse is first infected with herpesviruses in the eyelid, the mouse will soon have latent infection with them in the trigeminal ganglion. By removing such a ganglion from the mouse and then cultivating it in a test tube, it is possible to have the appearance of the viruses in the tissue so as to detect them. A bioassay examination was carried out by taking advantage of this nature of the virus, as will be described hereafter. 10,000,000 PFU of the F cell line of herpes simplex viruses 1 (multiplied in the vero cell) was pipetted into the eye of six-week-old ICR mice. Beginning on the next day, 500 g per day of JLS-18 was administered orally for five days. A group of mice treated this way and another group not were made up of ten mice each. After they were fed for three weeks after the treatment, their trigeminal ganglia were removed, and each of the ganglia was cultivated for three days in a 199 medium (Flow Corp.) to which 5 ml of 2% fetal calf serum had been added (for the reactivation of the latent viruses). After the cultivation, the tissues were rinsed with Dalbecco's phosphate-buffered physiological saline (Nissui Pharmaceutical Co.), and were minced in a 199 medium to which 2% fetal calf serum had been added, for the reactivated viruses to be extracted from the tissues.

Then these viruses were examined by applying the plaque assay system using vero cells derived from a monkey's kidney, as will be described from now on. Vero cells, which had been cultivated in an Eagle MEM (Nissui Pharmaceutical) to which 10% fetal calf serum had been added, were removed by using trypsin, and about 10,000 of them were placed in each hole in a 24 hole microplate, and then they were cultivated for two days so that they might adhere well to the plate. These cells were then applied for an hour to virus absorption using the virus extracts diluted stepwise to an appropriate concentration with an Eagle MEM to which 1% fetal calf serum had been added. After the cells were rinsed with Dalbecco's phosphate-buffered physiological saline, an Eagle MEM to which 1% fetal calf serum containing 0.2% agarose had been added was added to the cells in order to cultivate them for two days. The cultivated cells were inactivated with 10% formalin solution and stained with Methylene Blue, and the PFU quantity was counted under a microscope.

The result was that no virus was detected in the group treated with JLS-18 though reactivation of viruses in trigeminal ganglia was found in all the members of the group (10 mice) not treated with it with the virus concentration not less than 1000 PFU per ml. In addition to all the above, changing the administration of the agent from oral to abdominal did not give the experiment any different result.

Details of the results are shown in the following table.

JLS-18's activity for inhibiting latent infection virus reactivation is as follows:

(1) Oral administration

| Dose (μg per day) | Number of Mice | Positive as to Virus Infection (%) |
|---|---|---|
| 0 | 10 | 100 (10/10) |
| 100 | 10 | 30 (3/10) |
| 500 | 10 | 0 (0/10) |

(2) Abdominal administration

| Dose (μg per day) | Number of Mice | Positive as to Virus Infection (%) |
|---|---|---|
| 0 | 10 | 100 (10/10) |
| 30 | 10 | 60 (6/10) |
| 100 | 10 | 0 (0/10) |
| 500 | 10 | 0 (0/10) |

EXAMPLE 4

As described in Example 3, mice were infected with herpes simplex viruses and were fed four weeks without any treatment with medical agents so that they might receive latent infection. After their trigeminal ganglia were removed, the ganglia was cultivated for three days in the 199 medium to which 2% fetal calf serum had been added. 300 μg per ml of JLS-18 had been added to the medium for cultivating a group to be treated. After the cultivation, reactivated viruses were recovered from the ganglion tissues, as in Example 2. From the group not treated, not less than 10,000 PFU per ml of viruses were recovered, but from the group treated with JLS-18, no virus was.

EXAMPLE 5

JLS-18 preparations for oral administration were produced by wrapping 500 mg of the agent each.

EXAMPLE 6

100 g of JLS-18 ointment was produced by dissolving 3 g of JLS-18 in 10 ml of physiological saline, adding hydrophilic ointment to it and then kneading it.

A medical agent according to the present invention is for inhibiting the proliferation of herpesviruses and the reactivation of latently infecting herpesviruses and is, despite all these effects, for oral administration with ensured easy handling and high safety.

We claim:

1. A method of inhibiting the proliferation of herpesviruses or the recurrence of afflictions caused by their latent infection, comprising administering to a warm-blooded animal an effective amount of a composition comprising an inhibitor in combination with a pharmaceutically acceptable carrier, wherein the inhibitor comprises an active material obtained by the process comprising purifying an aqueous extract from cultured Lentinus edodes mycelia, said active material being a complex of water-soluble lignin, polysaccharide and peptide, having a ratio expressed in percent by weight of 65-75: 15-30: 10-20; wherein the peptide component of the active material has the following amino acid composition expressed in percent by weight based on the total weight of the peptide component

| Asx | 15.0-16.5 | Met | 0.3-0.7 |
|---|---|---|---|
| Thr | 6.5-7.2 | Ile | 3.8-4.9 |
| Ser | 6.5-7.3 | Leu | 4.9-6.6 |
| Glx | 15.0-17.5 | Tyr | 1.1-1.5 |
| Pro | 6.8-8.0 | Phe | 3.0-4.6 |
| Gly | 9.3-11.0 | Lys | 3.6-4.8 |
| Als | 7.3-8.8 | His | 2.3-2.9 |
| Val | 5.9-6.5 | Arg | 0.7-1.1 | said polysaccharide component having the following composition of sugars expressed in percent by weight based on the total weight of the polysaccharide component.

| Glucose | 35-55 |
|---|---|
| Xylose | 29-41 |
| Galactose | 2-7 |
| Arabinose | 12-20 |
| Mannose | 1-4. |

2. The method of claim 1, comprising administering the composition topically, said composition containing 0.01 to 1 percent by weight of said inhibitor.

3. The method of claim 1, comprising administering the composition orally at a dosage of from 10 mg to 10 g per day.

* * * * *